United States Patent [19]

Kawahara et al.

[11] Patent Number: 4,515,714

[45] Date of Patent: May 7, 1985

[54] METHOD FOR PURIFICATION OF HEPATITIS B VIRUS SURFACE ANTIGEN

[75] Inventors: Tetsuo Kawahara; Hiroshi Mizokami; Kyosuke Mizuno; Sadao Susumi, all of Kumamoto, Japan

[73] Assignee: Juridicial Foundation, The Chemo-Semo-Sero-Therapeutic Research Institute, Kumamoto, Japan

[21] Appl. No.: 586,702

[22] Filed: Mar. 6, 1984

[30] Foreign Application Priority Data

Mar. 9, 1983 [JP] Japan ................................. 58-39837
May 28, 1983 [JP] Japan ................................. 58-94495

[51] Int. Cl.³ .................. A61K 39/12; A61K 39/00; A61K 39/42; C07G 7/00
[52] U.S. Cl. ........................ 260/112 R; 260/112 B; 424/89; 424/86
[58] Field of Search ............ 260/112 B, 112 R; 424/89, 86

[56] References Cited

U.S. PATENT DOCUMENTS

| | | | |
|---|---|---|---|
| 3,842,061 | 10/1974 | Andersson et al. | 260/112 B |
| 3,920,625 | 11/1975 | Andersson et al. | 260/112 B |
| 4,138,287 | 2/1979 | Andersson et al. | 424/89 X |
| 4,160,019 | 7/1979 | Björklund | 260/112 B X |
| 4,168,300 | 9/1979 | Andersson et al. | 260/112 B X |
| 4,181,713 | 1/1980 | McAleer et al. | 260/112 B X |
| 4,434,093 | 2/1984 | Zolton et al. | 260/112 B |

OTHER PUBLICATIONS

Einarsson et al., Vox Sang. 35: 224–233, (1978).
Einarsson et al., Vox Sang. 41: 91–92, (1981).
Biochem. Biophys. Res. Comm., 102, No. 1, 1981, 449–457, Nilsson et al.
Proc. Nat. Acad. Sci., U.S.A., 72, No. 3, 1975, 1055–1058, Wilchek et al.

*Primary Examiner*—Howard E. Schain
*Attorney, Agent, or Firm*—Wegner & Bretschneider

[57] ABSTRACT

An improved method for the purification of hepatitis B virus surface antigen by column chromatography, which is characteristic in using as a gel for the chromatography a sulfuric acid ester of a crosslinked polysaccharide or cellulose which is obtained by sulfating a crosslinked polysaccharide or cellulose. Said method can give a highly purified hepatitis B virus surface antigen which is useful for the preparation of hepatitis B virus vaccine.

8 Claims, No Drawings

METHOD FOR PURIFICATION OF HEPATITIS B VIRUS SURFACE ANTIGEN

The present invention relates to a method for purification of hepatitis B virus surface antigen (hereinafter, referred to as "HBs antigen"). More particularly, it relates to a method for highly purifying HBs antigen by column chromatography using a sulfuric acid ester of a crosslinked polysaccharide or cellulose which is obtained by sulfating a crosslinked polysaccharide or cellulose.

Hepatitis B is usually induced by a hepatitis B virus having a diameter of 42 nm and containing a DNA type nucleic acid which infects via blood. This hepatitis B virus causes not only acute hepatitis but also chronic hepatitis, hepatocirrhosis and probably also hepatoma due to continuous infection with the virus. The hepatitis B is distributed worldwidely, and there are many latent virus carriers (hereinafter, merely referred to as "carrier") who hold the virus within the body for a long period of time without any subjective symptom. The number of the carriers may be about 2 to 3% of total population, i.e. 2 to 3 millions, in Japan, and about 10 to 15% of the residents in Southeast Asia and Africa, and it is assumed that about 200 million persons are the carrier of this virus in the world.

Effective prophylaxis of the hepatitis B is to administer a hepatitis B virus vaccine which is usually prepared by inactivation of a highly purified HBs antigen. Such a hepatitis B virus vaccine is effective not only for preventing people who are working in a circumstance highly infectious with the virus, such as persons who are engaged in medical work, from infection with the virus, but also for preventing generation of new carrier, and it is also expected to eliminate completely the hepatitis B from the earth.

The HBs antigen is retained on the surface of three kinds of hepatitis B virus or virus-like particles, i.e. Dane particle, which is hepatitis B virus per se having a diameter of 42 nm and containing therein 27 nm core having nucleic acid; baculiform particle having a diameter of 22 nm and a length of from several tens to several handreds nm which has no nucleic acid; and spherical particle having a diameter of 22 nm. An antibody against the HBs antigen is a protective antibody to the hepatitis B virus. Utilizing the function of producing the antibody against the HBs antigen in the body, the inactivated HBs antigen is used as an vaccine for hepatitis B.

The hepatitis B virus vaccine is usually prepared by isolating and purifying HBs antigen from blood plasma of hepatitis B virus carrier or culture broth or supernatant thereof obtained by culturing a microorganism having hepatitis B virus gene produced by genetic engineering, but the purification of HBs antigen must be done extremely efficiently, which requires high technique in the operation, and hence, it is very difficult to prepare the desired hepatitis B virus vaccine in an industrial scale.

The most commonly used purification method of HBs antigen is a density gradient centrifugation [cf. Vyas, G.N. et al., J. Immunology, 108, 1114 (1972); Hirshman, S.Z., Proceeding of National Academy of Science USA, 71, 3345 (1974)] However, this method requires to use a large amount of cesium chloride and sucrose and also to use a ultracentrifugal machine and also various rotors in accordance with the degree of purification and scale thereof, and hence, this method is not suitable in view of high cost.

It is also proposed to purify the HBs antigen by an affinity chromatography utilizing antigen-antibody reaction [cf. Houwen, B. et al., Journal of Immunological Method, 8, 185 (1975)]. This method shows high purification efficiency, but on the other hand, it requires a large amount of an HBs antiboty-positive human serum in order to obtain an HBs antibody for chromatography in order to produce the vaccine in an industrial scale, and further, the HBs antibody must be highly purified and must be bonded to a gel matrix with cyanogen bromide, etc. in order to prepare the affinity gel. Besides, according to the column chromatography using an affinity gel, because of weak binding between the HBs antibody and the gel, it is highly possible that the HBs antibody and HBs antibody-antigen reaction product are undesirably released from the gel during the elution step, which occasionally cause autoimmune disease and nephropathy due to contamination thereof into the vaccine.

It is also proposed to purify the HBs antigen by using an affinity gel which is prepared by conjugating a sulfonyl group-containing polysaccharide such as dextran sulfate, chondroitin sulfate, or heparin to Sepharose CL-4B (manufactured by Pharmacia in Sweden) or Sepharose CL-6B (manufactured by Pharmacia in Sweden) with cyanogen [cf. M. Einarsson et al., Vox Sang, 41, 91–97 (1981); U.S. Pat. No. 4,138,287; and Japanese Patent First Publication No. 114018/1977] However, the affinity gel used in this method must be prepared in complicated steps and further dangerous cyanogen bromide must be used, and hence, this method is not suitable for industrial production of the vaccine. Besides, the dextran sulfate, chondroitin sulfate or heparin used therein are expensive, and further, the binding of the sulfonyl group-containing polysaccharide to the carrier gel such as sepharose is limited and hence there is hardly obtainable an affinity gel having uniform quality which can highly purify HBs antigen. Moreover, when the sulfonyl group-containing polysaccharide and the carrier gel are bound with cyanogen bromide, the binding is comparatively weak and hence the polysaccharide may probably be released from the gel to contaminate the purified HBs antigen.

The present inventors have intensively studied an improvement of purification of HBs antigen by column chromatography with ease and low cost, and it has been found that a sulfuric acid ester of crosslinked polysaccharide or cellulose has a specific affinity with HBs antigen and is effective for isolation and purification of HBs antigen from biological materials such as blood serum and plasma in high purity and high yield and with ease.

An object of the present invention is to provide an improved method for purification of HBs antigen which is useful for industrial production of hepatitis B virus vaccine. Another object of the invention is to provide a method for high degree of purification of HBs antigen by column chromatography using a sulfuric acid ester of a crosslinked polysaccharide or cellulose. A further object of the invention is to provide a highly purified HBs antigen which is useful as hepatitis B virus vaccine. These and other objects and advantages of the present invention are apparent to persons skilled in the art from the following description.

The method of the present invention comprises subjecting an HBs antigen-containing solution, such as blood serum of hepatitis B virus carrier, a culture broth of a microorganism having hepatitis B virus gene prepared by genetic engineering, or a supernatant liquid of the culture broth, to column chromatography, which improvement comprises using as a gel for the chromatography a sulfuric acid ester of a crosslinked polysaccharide or cellulose.

The sulfuric acid ester of a crosslinked polysaccharide includes a sulfuric acid ester of polysaccharide, such as dextran, celluloses, agarose, which is crosslinked with a crosslinking agent, such as epichlorohydrin, dichlorohydrin, dibromohydrin, ethylene glycol bisepoxypropyl ether. The crosslinked polysaccharides are commercially available, for example, crosslinked dextrans such as Sephadex G-10, G-25, G-50, and G-100 (manufactured by Pharmacia in Sweden), crosslinked agaroses such as Sepharose Cl-2B, Cl-4B, and Cl-6B (manufactured by Pharmacia in Sweden), and crosslinked celluloses such as Cellulofine GCL-25, GCL-90 (manufactured by Chisso Corp. in Japan). The sulfuric acid ester of cellulose includes a sulfuric acid ester of crystalline cellulose or cellulose having crystalline area and non-crystalline area. These starting celluloses are commercially available, for example, Abicel (manufactured by Asahi Kasei in Japan), Cellulofine GC-15, GH-25, GC-100, or GC-200 (manufactured by Chisso Corp. in Japan). The sulfation of the crosslinked polysaccharide or cellulose can be carried out by a conventional method, for example, by treating a gel of the crosslinked polysaccharide or cellulose with chlorosulfonic acid, anhydrous sulfuric acid, or other sulfating agent in an organic solvent (e.g. pyridine). The degree of sulfation (content of the sulfonyl group) of crosslinked polysaccharide is usually in the range of 0.1 to 40%, preferably 10 to 40%, based on the weight of the crosslinked polysaccharide, and the degree of sulfation of cellulose is usually in the range of 0.1 to 7.0 preferably 0.1 to 5.0%, based on the weight of the cellulose. The sulfuric acid esters of crosslinked polysaccharides or celluloses are water-insoluble gel material and physically stable and are useful as a gel for chromatography. The sulfuric acid esters are used in various forms such as granules, fine granules, fine particles, preferably in the form of a spherical particle.

The procedure of purification of HBs antigen by column chromatography using the sulfuric acid ester of a crosslinked polysaccharide or cellulose is carried out in a similar manner to that in the conventional column chromatography. For instance, the method is carried out in the following manner. Firstly, a sulfuric acid ester of a crosslinked polysaccharide or cellulose (preferably, in the form of a spherical particle) is packed within a column, which is equilibrated with a suitable buffer solution having an ionic strength of about 0.001 to 1.0, preferably 0.05 to 0.2, and a pH range of 4 to 10, preferably 6 to 9, for example, McIlvaine's buffer solution (pH 5.0), 0.01 M phosphate buffered saline solution (pH 7.2), and 0.1 M sodium chloride-containing citrate buffer solution (pH 7.2). After the equilibration, an HBs antigen-containing solution to be treated is passed through the column in order to adsorb the HBs antigen onto the gel, followed by washing with the same buffer solution as used for the above equilibration. Thereafter, the adsorbed HBs antigen is eluted from the column by passing through the column a suitable buffer solution having an ionic strength larger than that of the buffer solution used for the above equilibration, i.e. an ionic strength of 0.1 to 5.0, preferably 0.4 to 3.0, and a pH range of 4 to 10, preferably 6 to 9, for example, 0.6 M sodium chloride-containing McIlvaine's buffer solution (pH 4-8), or 0.6 M sodium chloride-containing phosphate buffer solution (pH 6-9) to give the desired highly purified HBs antigen.

The purification method of the present invention can be applied to any HBs antigen-containing materials, such as biological materials (e.g. blood serum or plasma from hepatitis B virus carrier), a culture broth obtained by culturing a microorganism having a hepatitis B virus gene prepared by genetic engineering [cf. A. Miyanohara et al., Proc. Natl. Acad. Sci. USA, Vol. 80, pp. 1–5, January 1983; W.J. McAleer et al, Nature, Vol. 307, 12, January 1984; etc.], or a supernatant liquid of the culture broth.

According to the purification method of the present invention, the HBs antigen can be purified in a high degree, i.e. several tens of times of the purity of the starting HBs antigen and can be recovered in a high rate, such as more than 90% up to nearly 100%, because the sulfonyl group bonds directly to the crosslinked polysaccharide or cellulose in the sulfuric acid ester of a crosslinked polysaccharide or cellulose and hence it has a high content of sulfonyl group and shows excellent specific absorbability of HBs antigen.

The purification method of the present invention can easily be done with simple operation in an industrial scale without necessity of expensive agents and can give the desired purified HBs antigen in an industrial scale with lower cost. Besides, the gel used therein is very stable, and the product thus obtained has no impurities such as antigen-antibody reaction products which are occasionally observed in the conventional products. The purification method of the present invention may also be combined with the conventional purification techniques such as ultra-centrifugation or ion exchange chromatography, by which more excellent product can be obtained.

The present invention is illustrated by the following Preparations and Examples, but should not be construed to be limited thereto.

PREPARATION 1

To pyridine (200 ml) is added dropwise chlorosulfonic acid (11 ml) at below 0° C. After the addition, the mixture is heated to 65°–70° C. To the mixture is added epichlorohydrin-crosslinked dextran (Sephadex G-50, manufactured by Pharmacia) (7.5 g), and the mixture is stirred at 65°–70° C. for 4 hours. After the reaction, the reaction mixture is cooled and then neutralized with aqueous sodium hydroxide. The gel thus obtained is separated by filtration and washed well with 0.01 M phosphate buffered saline solution to give a crosslinked dextran sulfate.

PREPARATION 2

To a mixture of pyridine—chlorosulfonic acid (210 ml) prepared in the same manner as described in the above Preparation 1 is added dried product of crosslinked cellulose gel (Cellulofine GCL-25, manufactured by Chisso Corp.) (7.5 g), and the mixture is reacted at 65°–70° C. for 4 hours. After the reaction, the reaction mixture is cooled and neutralized with aqueous sodium hydroxide. The gel thus obtained is separated by filtration and washed well with 0.01 M phosphate buffered saline solution to give a crosslinked cellulose sulfate (7.2 g).

PREPARATION 3

To a mixture of pyridine—chlorosulfonic acid (210 ml) prepared in the same manner as described in the above Preparation 1 is added crosslinked agarose gel (Sepharose CL-6B, manufactured by Pharmacia) (30 ml) which is impregnated by pyridine, and the mixture is reacted at 65°–70° C. for 4 hours. After the reaction, the reaction mixture is cooled and neutralized with aqueous sodium hydroxide. The gel thus obtained is separated by filtration and washed well with 0.01 M phosphate buffered saline solution to give a crosslinked agarose sulfate (23 ml).

PREPARATION 4

To pyridine (600 ml) is added dropwise chlorosulfonic acid (117 g) at below 0° C. After the addition, the mixture is heated to 65°–70° C. To the mixture is added crystalline cellulose (Abicel for chromatography, manufactured by Asahi Kasei) (80 g), and the mixture is stirred at 65°–70° C. for 4 hours. After the reaction, the reaction mixture is cooled and then neutralized with 10% aqueous sodium hydroxide. The gel thus obtained is separated by filtration and washed well with 0.01 M phosphate buffer-aqueous sodium chloride mixture to give a cellulose sulfate gel.

PREPARATION 5

To pyridine (600 ml) is added dropwise chlorosulfonic acid (117 g) at below 0° C. After the addition, the mixture is heated to 65°–70° C. To the mixture is added crystalline cellulose gel (Cellulofine GC-15, manufactured by Chisso Corp.) (80 g), and the mixture is stirred at 65°–70° C. for 3 hours. After the reaction, the reaction mixture is cooled and neutralized with 10% aqueous sodium hydroxide. The gel thus obtained is separated by filtration and washed well with 0.01 M phosphate buffer-aqueous sodium chloride mixture to give a cellulose sulfate gel.

EXAMPLE 1

The crosslinked dextran sulfate gel obtained in the same manner as described in Preparation 1 is packed within a column (26.4 mm$\phi$ × 182 mm), and this is equilibrated with 0.05 M sodium chloride-containing 0.027 M McIlvaine's buffer solution (pH 7.41). An HBs antigen positive human serum [HBs antigen content, 31.3, $\mu$g/ml [radioimmuno assay method (AUSRIA II-125, manufactured by Dinabbott) (cf. Masami Kurokawa, Seiichi Saito; Japan. J. Med. Sci. Biol., 32, 47–52, 1979)], protein content, 70.0 mg/ml (Lowry's method), specific activity (HBs antigen content/protein content): 0.447](3.0 ml) is passed through the column. After washing well the column with the same buffer solution as above, the absorbed material is eluted with 0.6 M sodium chloride-containing 0.027 M McIlvaine's buffer solution (pH 7.38) to give a fraction (43.2 ml).

This fraction thus eluted has an HBs antigen content of 2.0, $\mu$g/ml, a protein content of 0.41 mg/ml and a specific activity of 4.88. The recovery rate of HBs antigen is 92.2%, and the degree of purification (specific activity of the eluted fraction/specific activity of the starting serum) is 10.9 times.

EXAMPLE 2

The crosslinked agarose sulfate gel obtained in the same manner as described in Preparation 3 is packed within a column (26.4 mm$\phi$ × 47.0 mm), and this is equilibrated with 0.05 M sodium chloride-containing 0.027 M citrate buffer solution (pH 7.36). An HBs antigen positive human serum [HBs antigen content, 62.5,$\mu$g/ml, protein content, 70.0 mg/ml, specific activity: 0.893](0.5 ml) is passed through the column, followed by washing well the column with the same buffer solution as above. The passed through solution and the washing liquid (totally 10.75 ml) have an HBs antigen content of 0.06/$\mu$g/ml, a protein content of 1,118 mg/ml and a specific activity of $5.4 \times 10^5$. The absorbed material is eluted with 0.6 M sodium chloride-containing 0.027 M citrate buffer solution (pH 7.23) to give a fraction (8.00 ml).

This fraction thus eluted has an HBs antigen content of 4.0, $\mu$g/ml, a protein content of 0.217 mg/ml and a specific activity of 18.43. The recovery rate of HBs antigen is 102.4%, and the degree of purification is 20.6 times.

EXAMPLE 3

The crosslinked cellulose sulfate gel obtained in the same manner as described in Preparation 2 is packed within a column (26.4 mm$\phi$ × 105 mm), and this is equilibrated with 0.05 M sodium chloride-containing 0.027 M citrate buffer solution (pH 7.39). An HBs antigen positive human plasma (20 ml) which is diluted to double volume with the same buffer solution as above is passed through the column. After washing well the column with the same buffer solution as above, the absorbed material is eluted with 0.6 M sodium chloride-containing 0.027 M citrate buffer solution (pH 7.39). The results are shown in Table 1.

As is shown in Table 1, the HBs anitgen is almost recovered in the eluted fraction, and both of the specific activity and the degree of purification are increased to about 17 times.

TABLE 1

| Material | Volume (ml) | HBs antigen*[1] ($\mu$g/ml) | Protein (mg/ml) | Recovery rate of HBs antigen | Specific activity*[2] | Degree of purification |
| --- | --- | --- | --- | --- | --- | --- |
| Plasma | 20.0 | 70.5 | 70.0 | 100.0 | 1.01 | 1.00 |
| Passed through solution*[3] | 34.0 | 0.98 | 14.2 | 2.4 | 0.069 | 0.068 |
| Eluate | 40.8 | 36.0 | 2.09 | 104.2 | 17.22 | 17.10 |

*[1]It is measured by radioimmuno assay (AUSRIA II-125, manufactured by Dinabbott) [cf. Masami Kurokawa, Seiichi Saito, Japan. J. Med. Sci. Biol., 32, 47–52 (1979)]
*[2]The specific activity = amount of antigen ($\mu$g)/amount of protein (mg).
*[3]This includes both of a part of the passed through solution and a part of the washing liquid which contain HBs antigen.

A part of the purified HBs antigen obtained above was subjected to a ultracentrifugal analysis. That is, the sample was centrifuged at 40,000 rpm for 15 hours with Hitachi 70 P-72 unltracentrifuge and RPS 40 T rotor with forming cesium chloride density gradient, by which the HBs antigen showed a sharp peak at $\rho = 1.2$. This means that the HBs antigen is pure and single.

REFERENCE EXAMPLE 1

The crosslinked cellulose gel (Cellulofine GCL-25) is packed within a column (26.4 mm$\phi$ × 120 mm), and this is equilibrated with 0.05 M sodium chloride-containing 0.027 M citrate buffer solution (pH 7.40). An HBs antigen positive human plasma (20 ml) (the same lot of the plasma as used in Example 3) which is diluted to double volume with the same buffer solution as above is passed through the column, followed by washing well the column with the same buffer solution as above. The absorbed material is eluted with 0.6 M sodium chloride-containing 0.027 M citrate buffer solution (pH 7.40). 98.2% of the HBs antigen is recovered in the passed through fraction, and almost (96.7%) of the protein is also found in the passed through fraction. No absorption peak is observed in the eluted fraction, and the HBs antigen titer is less than 1 : 2 RPHA (reverse passive hemagglutination). Thus, the HBs antigen is entirely not purified.

EXAMPLE 4

The crosslinked cellulose sulfate gel obtained in the same manner as described in Preparation 2 is packed within a column (26.4 mm$\phi$ × 125 mm), and this is equilibrated with 0.01 M phosphate buffered saline solution (pH 7.20).

Separately, an HBs antigen positive human serum is salted out with ammonium sulfate, purified with a density gradient zonal centrifuge (Hitachi 70 P-72) (under the conditions of sucrose density gradient: 10–45% by w/w, 30,000 rpm, 20 hours, using Hitachi RPZ-35-T rotor; and sucrose density gradient: 20–50% by w/w, 42,000 rpm, 20 hours, using Hitachi RPZ-48 T rotor), and then dialyzed against 0.01 M phosphate buffered saline solution to give an HBs antigen-containing solution (40 ml) [HBs antigen content, 62.5 μg/ml, normal human serum: positive in immunoelectro syneresis).

The HBs antigen thus treated is passed through the above column. After washing the column with 0.01 M phosphate buffered saline solution (pH 7.20), the absorbed material is eluted with 0.6 M sodium chloride-containing 0.01 M phosphate buffer solution (pH 7.20) to give a fraction (12.0 ml).

This fraction thus eluted has an HBs antigen content of 200 μg/ml, and no plasma protein other than HBs antigen is observed by immunoelectro syneresis. Thus, the HBs antigen is almost completely purified, and the recovery rate thereof is 96.0%.

EXAMPLE 5

The cellulose sulfate gel obtained in the same manner as described in Preparation 4 is packed within a column (26.4 mm$\phi$ × 105 mm), and this equilibrated with 0.05 M sodium chloride-containing 0.027 M citrate buffer solution (pH 7.40). An HBs antigen positive human serum [HBs antigen content, 50.78 μg/ml, protein content, 74.5 mg/ml, specific activity: 0.68](10 ml) which is diluted to three folds volume with the same buffer solution as above is passed through the column. After washing well the column with the same buffer solution as above, the absorbed material is eluted with 0.6 M sodium chloride-containing 0.027 M citrate buffer solution (pH 7.20) to give a fraction (45.0 ml).

This fraction thus eluted has an HBs antigen content of 10 μg/ml, a protein content of 1.25 mg/ml and a specific activity of 8.0, the recovery rate of HBs antigen is 88.6%, and the degree of purification (specific activity of the eluted fraction/specific activity of the starting serum) is 11.7 times.

EXAMPLE 6

The cellulose sulfate gel obtained in the same manner as described in Preparation 5 is packed within a column (26.4 mm$\phi$ × 105 mm), and this is equilibrated with 0.05 M sodium chloride-containing 0.027 M citrate buffer solution (pH 5.00). An HBs antigen positive human serum [HBs antigen content, 50.78 μg/ml, protein content, 74.5 mg/ml, specific activity: 0.68](16 ml) which is diluted to three folds volume with the same buffer solution as above is passed through the column. After washing well the column with the same buffer solution as above, the absorbed material is eluted with 0.6 M sodium chloride-containing 0.027 M citrate buffer solution (pH 5.00) to give a fraction (52 ml).

This fraction thus eluted has an HBs antigen content of 15, μg/ml, a protein content of 2.12 mg/ml and a specific activity of 7.08. The recovery rate of HBs antigen is 96.0%, and the degree of purification is 10.4 times.

EXAMPLE 7

The cellulose sulfate gel obtained in the same manner as described in Preparation 5 is packed within a column, and this is equilibrated with 0.05 M sodium chloride-containing 0.027 M McIlvaine's buffer solution (pH 7.20). An HBs antigen positive human plasma (20 ml) which is diluted to three folds volume with the same buffer solution as above is passed through the column. After washing well the column with the same buffer solution as above, the absorbed material is eluted with 0.6 M sodium chloride-containing 0.027 M McIlvaine's buffer solution (pH 7.20). The results are shown in Table 2. As is shown in Table 2, the HBs antigen is almost recovered in the eluted fraction, and the degree of purification is about 16 times.

TABLE 2

| Material | Volume (ml) | HBs antigen*[1] (g/ml) | Protein (mg/ml) | Recovery rate of HBs antigen | Specific activity*[2] | Degree of purification |
|---|---|---|---|---|---|---|
| Serum | 20.0 | 32.5 | 72.0 | 100.0 | 0.45 | 1.00 |
| Passed through solution*[3] | 120.0 | 0.36 | 7.8 | 6.6 | 0.046 | 0.10 |
| Eluate | 64.0 | 9.8 | 1.4 | 96.5 | 7.0 | 15.6 |

*[1] It is measured by radioimmuno assay (Auseria II-125, manufactured by Dinabbott) [cf. Masami Kurokawa, Seiichi Saito, Japan. J. Med. Sci. Biol., 32, 47–52 (1979)]
*[2] The specific activity = amount of antigen (μg)/amount of protein (mg).
*[3] This includes both of a part of the passed through solution and a part of the washing liquid which contain HBs antigen.

What is claimed is:

1. In a method for the purification of hepatitis B virus surface anitgen comprising subjecting a heptitis B virus surface anitgen-containing solution to column chromatography, the improvement comprising using a sulfuric acid ester of a cross-linked polysaccharide or cellulose as a gel for the chromatography, said sulfuric acid ester being prepared by treating a gel of crosslinked polysaccharide or cellulose with a sulfating agent in an organic solvent.

2. The method according to claim 1, wherein the sulfuric acid ester of a crosslinked polysaccharide is a member selected from the group consisting of a crosslinked celluluse sulfate, a crosslinked agarose sulfate, and a crosslinked dextran sulfate, which is prepared by treating a gel of crosslinked cellulose, crosslinked agarose or crosslinked dextran with a sulfating agent in an organic solvent.

3. The method according to claim 2, wherein the cross-linked cellulose sulfate is an epichlorohydrin-crossed-linked cellulose sulfate which is prepared by treating a gel of epichlorohydrin-crosslinked cellulose with a sulfating agent in an organic solvent.

4. The method according to claim 2, wherein the cross-linked agarose sulfate is an epichlorohydrin-cross-linked agarose sulfate which is prepared by treating a gel of epichlorohydrin-crosslinked agarose with sulfating agent in an organic solvent.

5. The method according to claim 2, wherein the cross-linked dextran sulfate is an epichlorohydrin-cross-linked dextran sulfate which is prepared by treating a gel of ephichlorohydrin-crosslinked dextran with sulfating agent in an organic solvent.

6. The method according to claim 1, wherein the sulfuric acid ester of cellulose is a sulfuric acid ester of a cellulose selected from crystalline cellulose and a cellulose having a crystalline area and onocrystalline area, which is prepared by treating a gel of the cellulose with a sulfating agent in an organic solvent.

7. A method for the purification of hepatitis B virus surface antigen, which comprises packing a gel of a sulfuric acid ester of a crosslinked polysaccharide or cellulose within a column, equilibrating the column with a buffer solution of an ionic strength of 0.001 to 1.0 and a pH range of 4 to 10, passing through the column a hepatitis B virus surface antigen-containing solution, and eluting the absorbed hepatitis B virus surface antigen with a buffer solution of an ionic strength of 0.1 to 5.0 which is larger than that of the buffer solution for the equilibration dnd a pH range of 4 to 10, said sulfuric acid ester being prepared by treating a gel of cross-linked polysaccharide or cellulose with a sulfating agent in an organic solvent.

8. The method according to claim 1, wherein the sulfating agent is a member selected from the group consisting of chlorosulfonic acid and anhydrous sulfuric acid.

* * * * *